United States Patent [19]

McMillan

[11] Patent Number: 4,910,402

[45] Date of Patent: Mar. 20, 1990

[54] APPARATUS AND METHOD FOR MEASURING A PROPERTY OF A LIQUID

[76] Inventor: Norman McMillan, Whitebutts, Killeshin Rd., Graiquecullen, Carlow, County Carlow, Ireland

[21] Appl. No.: 175,859

[22] Filed: Mar. 31, 1988

[30] Foreign Application Priority Data

Apr. 10, 1987 [IE] Ireland .................................... 947/87

[51] Int. Cl.$^4$ ............................................. G01N 21/49
[52] U.S. Cl. .................................... 250/341; 250/574; 250/576; 250/227.29; 356/445
[58] Field of Search ............. 250/227, 341, 576, 461.2, 250/574; 356/440, 432 T, 36, 445, 244; 324/438

[56] References Cited

U.S. PATENT DOCUMENTS

| | | | |
|---|---|---|---|
| 3,734,622 | 5/1973 | Adler | 250/576 |
| 4,006,360 | 2/1977 | Mueller | 250/461.2 |
| 4,049,970 | 9/1977 | Ford | 250/461.2 |
| 4,303,343 | 12/1981 | Patel et al. | 356/432 T |
| 4,643,580 | 2/1987 | Gross et al. | 356/440 |

*Primary Examiner*—Carolyn E. Fields
*Attorney, Agent, or Firm*—Brumbaugh, Graves, Donohue & Raymond

[57] ABSTRACT

An apparatus for measuring a property of a liquid comprises at least one guide for electromagnetic radiation, means for directing electromagnetic radiation into the guide, means for providing at least one drop of liquid in contact with the guide at a position where radiation from the guide can enter the drop, and means for deriving a signal which is a function of the interaction of the radiation with the liquid of the drop.

13 Claims, 5 Drawing Sheets

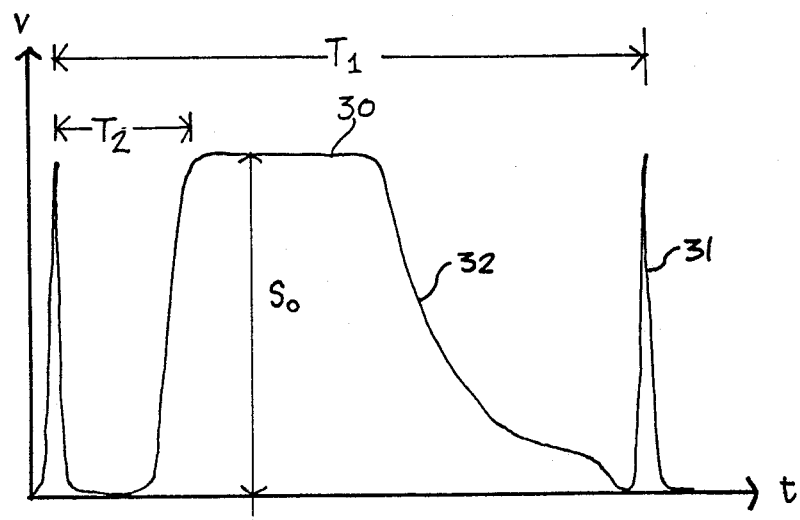
Fig_4.
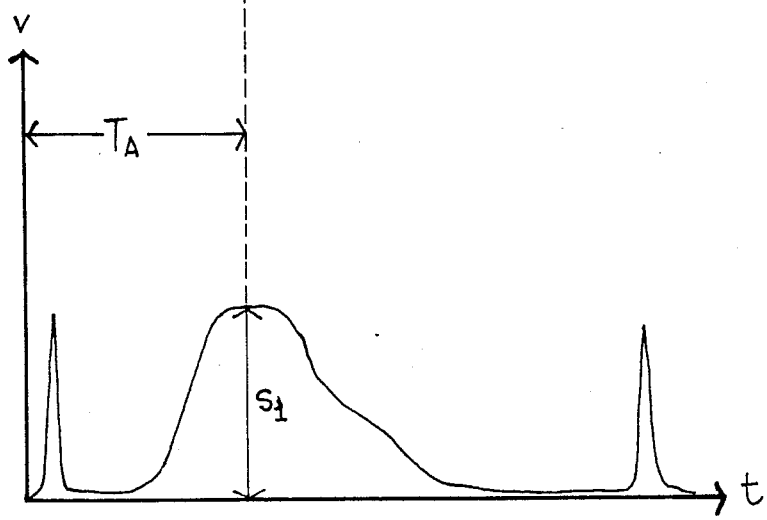
Fig_5.

APPARATUS AND METHOD FOR MEASURING A PROPERTY OF A LIQUID

The invention relates to an apparatus and method for measuring a property of a liquid.

According to the invention there is provided an apparatus for measuring a property of a liquid, comprising at least one guide for electromagnetic radiation, means for directing electromagnetic radiation into the guide, means for providing at least one drop of liquid in contact with the guide at a position where radiation from the guide can enter the drop, and means for deriving a signal which is a function of the interaction of the radiation with the liquid of the drop.

The liquid may be formed as a static drop suspended at the free end of the radiation guide, e.g. a light guide, or it may be a dynamic drop—one of a succession of drops allowed to drip from the end of the guide. Thus one can perform measurements on small volumes, or continuously monitor a liquid in a flow process by bleeding off sample droplets for measurement.

The electromagnetic radiation may be any such radiation which can be guided along a radiation guide to the drop, and may be continuous, pulsed or otherwise modulated to facilitate the particular analysis being performed.

The electromagnetic radiation supplied to the drop along the guide may be combined with other electromagnetic energy or other forms of energy (for example acoustic energy) also supplied to the drop, either applied along the guide, by an external field or by any other method of energising the drop. Such other forms of energy may be used to pump a process in or outside the drop in order to change the conditions relating to the measurement being performed.

The temperature or other ambient conditions may be changed in any desired manner to vary the physical conditions for the measurement or as experimental control variables.

The signal which is a function of the interaction of the liquid with the radiation may be derived by any device appropriate to the particular analysis, and may comprise a dedicated instrument or system or an instrument or system with general applications.

Most simply, the signal is derived by measuring the level of radiation reflected internally of the drop into the same or a further radiation guide. However, other forms of sensor or probe may be used.

The invention further provides a method for measuring a property of a liquid, comprising providing at least one guide for electromagnetic radiation, directing electromagnetic radiation into the guide, providing at least one drop of liquid in contact with the guide at a position where radiation from the guide can enter the drop, and deriving a signal which is a function of the interaction of the radiation with the liquid of the drop.

Although the invention is described herein using optical fibres as radiation guides, the latter could be formed by other radiation-guiding means such as capillary tubes or other radiation guides.

Furthermore, while the invention is described herein in terms of supplying the drop to the radiation guide by gravity feed, other techniques are possible. For example, drop could be formed and suspended in an electric field, and brought to the measuring position from below, or from the side. This would also permit making some measurements while the drop is approaching the guide.

Also, the drop need not be attached to the end of the guide, as described herein. It can be attached to any part of the guide where the radiation is capable of passing into it, for example, at an intermediate position on the guide where the radiation is coupled into the drop via the evanescent wave.

The invention can be used inter alia to measure a wide range of physical, chemical, electrical, opto-acoustical and other properties of the liquid, either singly or in any combination. These include:
1. Refractive index.
2. Surface tension.
3. Specific gravity.
4. Viscosity (absolute or kinematic).
5. Turbidity.
6. Absorption or chemical composition.
7. Fluorescence.
8. pH.
9. Conductivity or ion type.
10. Opto-acoustical properties.
11. Adhesion or other mechanical properties.
12. Pressure head.
13. Liquid volume.
14. Any other properties, such as humidity, which may condition the drop and so be indirectly measured.

Embodiments of the invention will now be described, by way of example, with reference to the accompanying drawings, in which:

FIG. 4 is a voltage/time diagram of a typical signal produced by the detector circuit of FIG. 1 for a transparent liquid with low absorption;

FIG. 5 is a similar voltage/time diagram for a liquid having significant absorption;

Figure 1:
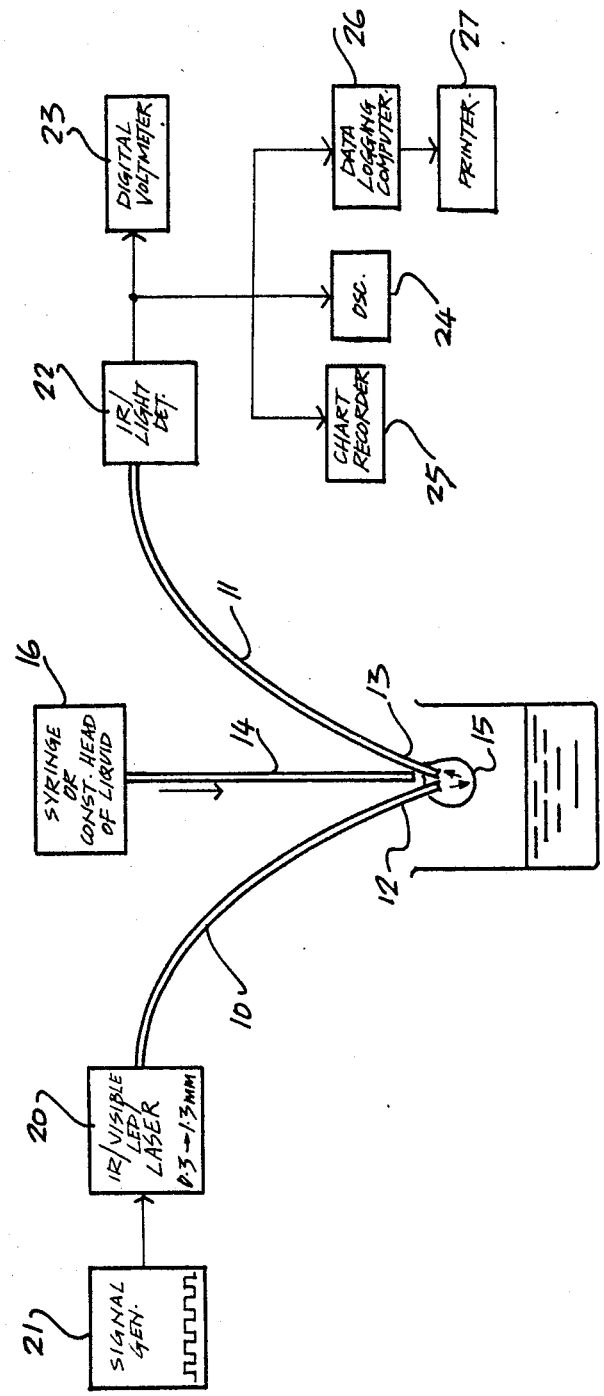
FIG. 1 is a schematic diagram of an embodiment of an apparatus for performing the invention.

Referring to FIG. 1, first and second radiation guides in the form of optical fibres 10 and 11 are brought close together at their downwardly facing free ends 12 and 13 respectively. The free end of a liquid feed pipe 14 is also brought into close proximity to the ends 12 and 13 of the optical fibres, so that liquid supplied by the latter can for a drop 15, or a succession of drops, at the ends of the fibres.

The pipe 14 may be supplied by a syringe type plunger so that a single static drop 15 may be formed, or alternatively the pipe 14 may be fed by a constant head of liquid from a constant head apparatus so that a succession of reproducible drops 15 are fed under gravity to the ends 12 and 13 of the optical fibres and allowed to drip therefrom. These alternatives are schematically shown at 16, and are so well known that no detailed description is thought necessary.

Figure 2:
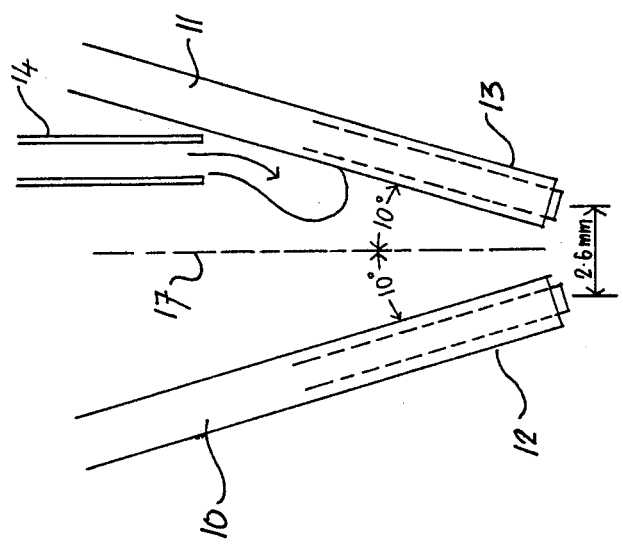
FIG. 2 is an enlarged view of the downwardly facing free ends of the optical fibres shown in FIG. 1.

Referring to FIG. 2, which shows the free ends of the fibres 10 and 11 and the pipe 14 to an enlarged scale, at their free ends 12 and 13 the axes of the fibres 10 and 11 are disposed symmetrically on either side of a vertical plane 17 at an angle of 18° to 22° with respect to one another, and preferably at an angle of 20° as shown.

The fibres may be polymethyl methacrylate fibres with an actual fibre core diameter (i.e. excluding the outer casing) of 1 mm. The centres of their lower ends are spaced apart by about 2.6 mm as shown. The fibres may be step index fibres. Graded index or monomode fibres may be used although it will be readily understood that in such cases other geometries must be used for optimum working. It will be noted that the pipe 14 is offset from the centre plane 17 between the fibres 10 and 11, so that the liquid flows down the fibre 11 to the ends 12 and 13.

Figure 3:
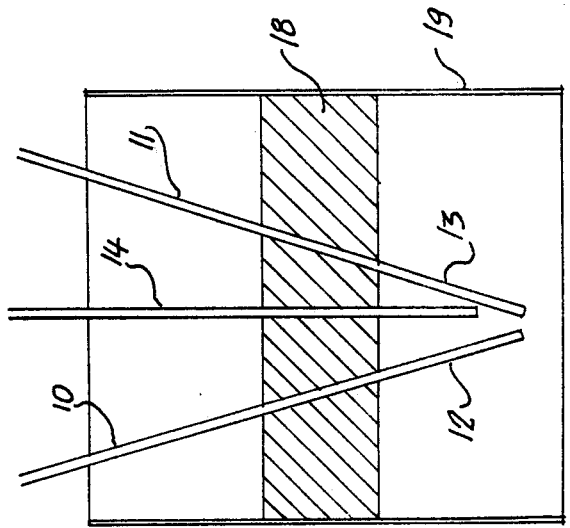
FIG. 3 illustrates how the fibres may be securely supported in the position shown in FIG. 2 for handling and protection.

In order to securely support the fibres 10 and 11 and the pipe 14 in their relative positions shown in FIG. 2, their lower free ends are fixed in epoxy resin 18 in a glass cylinder 19, FIG. 3, the lower end of the cylinder extending slightly below the free ends 12 and 13 of the fibres for protection and handling.

Referring again to FIG. 1, infra-red (IR) or visible radiation in the range 0.3 um to 1.3 um is supplied by an LED, solid state laser or other radiation source 20 which directs radiation into the end of the optical fibre 10 remote from the drop 15, and such radiation travels along the fibre 10 to the drop 15.

The radiation may be continuous, varied in a cyclic manner, or otherwise varied to facilitate a particular measurement. In the present case the radiation source 20 is a "Honeywell Sweet Spot" pulsed LED operated in the range 50 Hz to 10 KHz by a square wave signal generator 21. The generator 21 provides for stable operation of the LED 20, as well as providing advantages in measurement to be described.

Radiation from the source 20 travels along the fibre 10 to reach the drop 15 and is reflected internally of the drop 15 to travel up to the second optical fibre 11 to a detector circuit 22 (e.g. an IR detector or light-dependent resistor) where the level of the reflected radiation is measured. For example, the detector 22 may be an infrared phototransistor configured in a simple potential divider circuit with approximately 9 volts supply. The detected output level is supplied to one or more of a digital voltmeter 23, a storage oscilloscope 24, a chart recorder 25 and a data logging computer 26 with associated printer 27.

In the case of a liquid drop held suspended at the ends 12 and 13 of the optical fibres, i.e. a static drop, the level of radiation reflected up on the optical fibre 11, as measured by the digital voltmeter 23, is directly proportional so the refractive index of the liquid, assuming constant drop size and absorbance.

It was found in the static mode by experiment that the most reproducible results were obtained by careful tilting of the apparatus out of the vertical plane (i.e. out of the plane of FIG. 2) and adjusting the drop size, using the syringe, to obtain a maximum signal. It will be noted that the modulation of the IR source 20 by the generator 21 is not registered by the digital voltmeter 23.

Thus, by taking voltmeter reading for liquids of known refractive index and plotting these as a straight line graph of refractive index against the voltmeter reading, the refractive index of any other liquid can be determined from the graph by its voltmeter reading.

Other properties of the liquid can also be determined by the static method, for example, absorbance (concentration of dissolved chemicals in a given solvent).

Conventionally, absorbance is measured using a cuvette. Light is passed through the cuvette, and the absorbance A is given by $A = \log(I_0/I)$ where $I_0$ is the incident intensity and I is the intensity after passing through the cuvette. Since $A = E.c.l$ where E = extinction coefficient, c = concentration and l = distance travelled by the light through the cuvette, c (concentration) can be determined from A, since E can be obtained from reference books and l is known for the cuvette.

However, cuvettes are subject to variations in tolerance, and since a drop 15 can be reproduced almost exactly on the present apparatus, it can therefore effectively constitute an almost ideal cuvette. Thus by plotting A against c for liquids of known concentration, where in this case $I_0$ = input level to the drop and I = output level as measured by the digital voltmeter 23, a calibration curve can be obtained.

In the case of dynamic drops, FIG. 4 shows (for a relatively transparent liquid with low absorption) the voltage/time diagram as each drop falls from the ends of the optical fibres 10 and 11 into the beaker 28. This diagram will be produced by the oscilloscope 24, the chart recorder 25, and the printer 27 of the computer 26. The broad peak 30 corresponds to the growth of the drop, and the final narrow peak 31 is from the ends of the optical fibres.

It is to be understood that the diagram used in the present analysis is one where the height of the narrow peak 31 is as close to the height of the broad peak 30 as possible, and this is achieved by tilting the apparatus as previously described until the best results are achieved.

From such a diagram, the time period $T_2$ can be used to determine the refractive index of the liquid using a calibration procedure. Thus, if n (refractive index) is plotted against $T_2/V$ (where V—volume per second) for a number of liquids of known refractive index, a calibration curve is obtained which can be used to determine the refractive index of liquids whose refractive index is not known.

Further, the overall cycle period $T_1$ of the diagram is a function of the surface tension of the liquid and the kinematic viscosity in a gravity feed constant head apparatus. The kinematic viscosity can be determined by a calibration technique from the slope 32, and the surface tension can then be determined from the kinematic viscosity and $T_1$.

The width of the peak 31 at half its amplitude is a measure of the specific gravity of the liquid.

Other properties can be determined by processing the data from the trace, either manually from the trace or by suitably programming the computer 26. In this connection, the square wave superimposed on the trace assists in ascertaining the various measuring points required. Differentiation and double differentiation will also help to identify points of interest, and if necessary, any modulation applied by the generator 21 (FIG. 1) can be filtered out before this is done.

FIG. 5 shows how the trace of FIG. 4 is modified by absorption. For chemical analysis, an analysis time $T_A$ is fixed and the height of the signal $S_1$ for an absorbing liquid can be measured for different concentrations at one measurement wavelength. A graph of absorbance $A = \log(S_0/S_1)$ can be plotted against concentration and from this calibration graph the concentration of an unknown solution can be determined.

Alternatively, chemical analysis may be performed by integrating the detected signal, i.e. measuring the area under the trace during the cycle period $T_1$. The area will decrease with increasing concentration.

The analysis of turbidity can be done in a similar fashion by measuring the decrease in $S_o$ with increasingly turbid solutions.

If the liquid is fluorescent, then an excitation wavelength, such as UV or blue, can be used and the signal measured at the detector 22 which in this case has a monochromatic filter at a longer wavelength, such as orange, placed in front of it. The measurement would be done by the standard fluorescent methods of plotting this signal against the concentration of the fluorescent substance to obtain a calibration graph from which an unknown can be determined.

Figure 6:
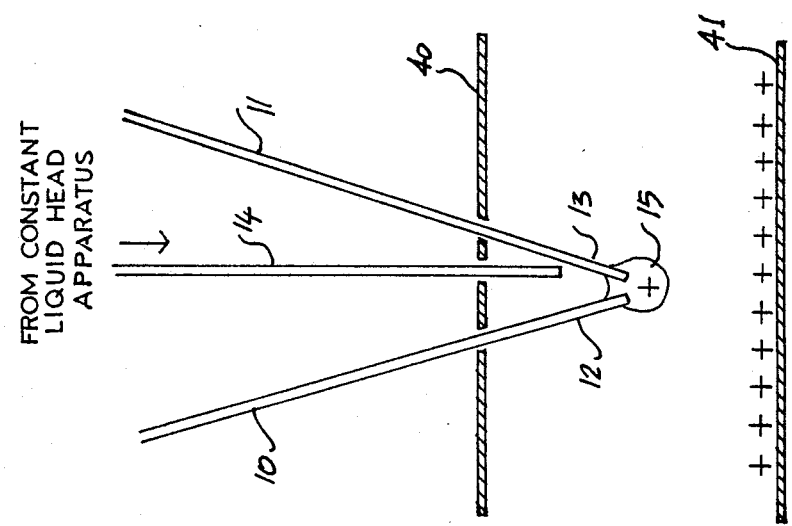
FIG. 6 shows a form of the apparatus for measuring pH.

Referring now to FIG. 6, the apparatus is shown modified to measure pH. In this case, a pair of large area capacitor plates 40 and 41 are disposed respectively one above and one below the free ends 12 and 13 of the optical fibres, and are separated from the latter by 4 to 4 cm.

Each drop 15 becomes charged as it detaches from the ends of the fibres, usually positively under normal atmospheric conditions, which charges up the lower plate 41 of the capacitor. Thus the drops are increasingly repelled, so that $T_1$ increases until a maximum is reached where the additional charge from each drop equals the leakage from the plate 41. This maximum value of $T_1$ gives a measure of the pH value of the liquid.

An AC or DC voltage supply can be connected across the plates of the capacitor to vary $T_1$, and these variations can be related to the electrical properties of the liquid. Likewise, the liquid feed could be charged to vary $T_1$.

The pH of the solution can be obtained by placing the drop in an electric field and the drop time, $T_1$, can be made to vary according to the voltage developed on the capacitor.

A voltage will appear by self charging of the capacitor due to the rupture of the drop from the body of supporting liquid, and this will lead to an increase in the drop time, which itself will be a function of the electrical properties of the liquid. The electrical condition of the atmosphere can be monitored via the simple fibre drop analyser by connecting the liquid drop feed to a voltmeter and allowing the induced change on the drop to continue to carry away change until the equilibrium situation is obtained when the voltage of the feed equates with the voltage of the potential of the surrounding air.

Figure 7:
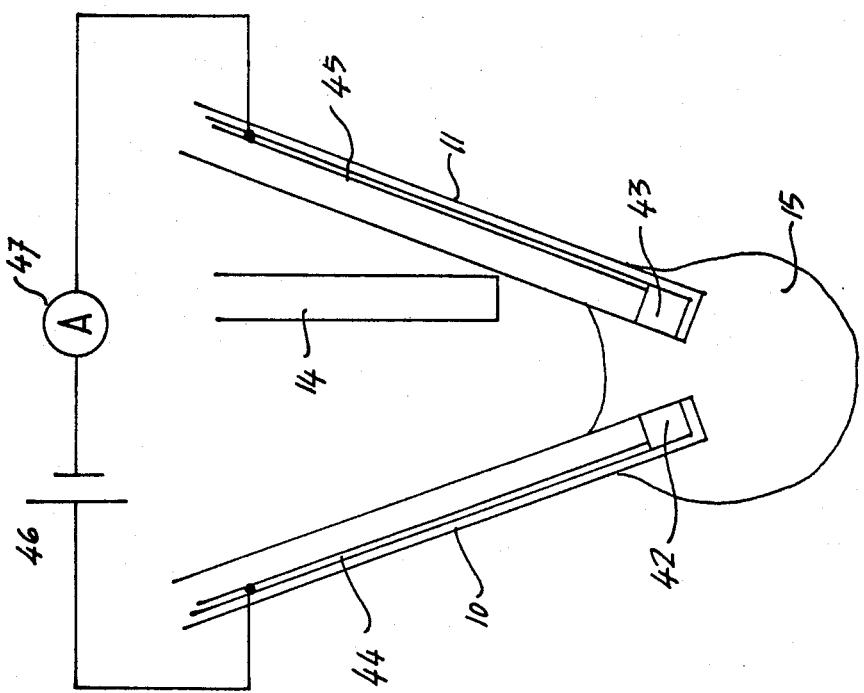
FIG. 7 shows a form of the apparatus for measuring conductivity.

Referring to FIG. 7, the conductivity of a liquid can be measured by providing respective electrodes 42 and 43 adjacent the free ends of each fibre 10 and 11 respectively. Respective conductors 44 and 45 extending from each electrode along the exterior of each fibre in the direction away from the free ends permit connection of the electrodes 42 and 43 to an external electrical circuit comprising, in this case, a constant voltage supply 46 and an ammeter 47.

An alternative bubble analysis can be devised to work on the principle above, with downward facing and inwardly pointing fibres directed at a liquid surface to carry out the analysis on an exploding bubble released from the bottom of a container.

The foregoing describes just some of the many uses of the apparatus described.

For example, the apparatus can be used as a rain gauge. If the syringe or constant head apparatus 16 is replaced by, for example, a funnel open at the top to rainfall and whose bottom is connected to the pipe 14, the rainfall may be measured by counting the total number and/or frequency of drops. This measurement may be effected, for example, by counting the broad peaks 30 of the trade in the computer 26 or in a separate counter.

Also, the time $T_1$ could be used to monitor pressure head where this was important for control purposes.

The dynamic properties of a liquid may be examined with the drop in situ. Thus the drop can be caused to oscillate, while remaining on the ends of the fibres, by the application of varying electromagnetic or electrostatic fields, or by mechanical vibration. In this case the trace would have symmetrical peaks 30, and no peaks 31. The period, amplitude and phase of the oscillations, as measured by the detector 22, would give information regarding the mechanical and/or electrical properties of the liquid depending on the circumstances of the procedure.

While the above has shown an arrangement where there are two optical fibres, a source fibre and a receiving fibre, other geometries for the fibre optics or other light guides are possible.

Figure 8:
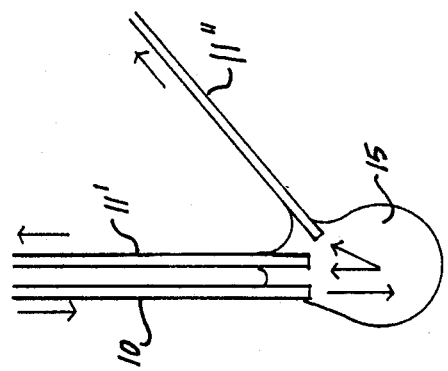

Thus, as seen in FIG. 8, the source fibre 10 injects light into a drop which couples into two receiving optical fibres 11' and 11'' which can detect individually the quantity of radiation coupled to a respective detector at the end of the fibre, or it may be used to compare the difference between the light coupled to produce a differential analyser.

Figure 9:
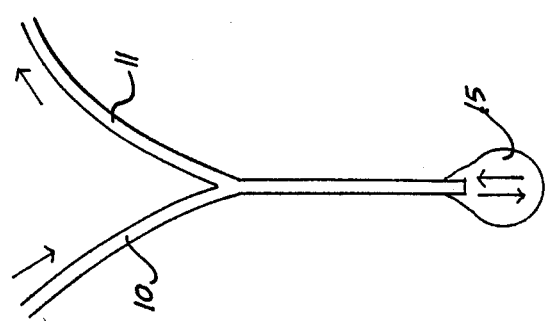

In FIG. 9, a single bifurcated optical fibre is used, the left hand branch 10 constituting the source, and the right hand branch 11 the receiver. This design produces an increased coupling to the receiving fibre when the fibre is tilted, but one which is asymmetric having a preferential clockwise tilt. A multi-fibre system could also be used to carry many wavelengths into the drop to enable, for example, the chemical analysis of several components simultaneously.

Figure 10:
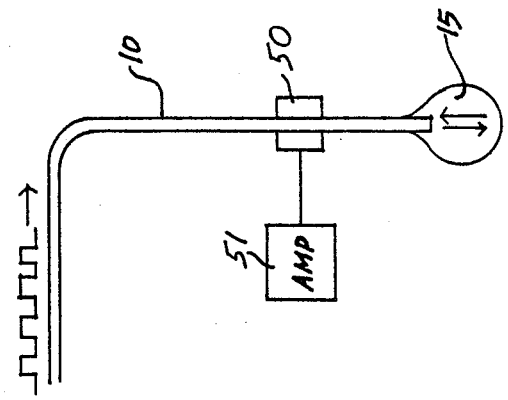
FIGS. 8 to 10 illustrate alternative light guide and detection arrangements.

Finally, in FIG. 10, a single fibre 10 may be used, and detection is accomplished by a sensitive opto-acoustical microphone 50 and amplifier 51 which detects the sound produced in the sample by the pulsed source (17, 18 in FIG. 1). In this case the sample liquid may be opaque and does not need to transmit radiation.

The commercial applications of the apparatus are many:

1. A system monitor and controller for an industrial flow process.
2. A water monitor for monitoring a selection of quantities for a reservoir or industrial process.
3. A household water quantity and quality meter.
4. A rain gauge to measure the properties of rain water, e.g. acid rain.
5. A laboratory liquid analyser, either dedicated for a specific application or general purpose.
6. A medical or clinical drip analyser.
7. A saccharimeter.

Naturally the use of an opto-acoustical microphone is not limited to the embodiment of FIG. 10 but could be used more generally, for example, in relation to the receiving fibre 11 in FIG. 1.

I claim:

1. An apparatus for measuring a property of a liquid, comprising:
    at least one elongated electromagnetic radiation guide having an upwardly-facing end and a downwardly-facing free end, means for directing electromagnetic radiation into the upwardly-facing end of said at least one guide for guidance to the free end thereof, means for supplying liquid to be measured including means for causing the liquid to flow by gravity down a surface and to form at least one drop of said liquid at the free end of said at least one guide at a position where radiation from the at least one guide can enter said at least one drop, and means for detecting the amplitude of radiation reflected internally of said at least one drop for deriving a signal which is a function of the interaction of the radiation with the liquid of the at least one drop.

2. An apparatus according to claim 1, wherein said means for detecting comprises a detector coupled to the upwardly-facing end of said at least one radiation guide for measuring the amplitude of radiation reflected from said at least one drop into said at least one guide.

3. An apparatus according to claim 1, wherein said apparatus further includes a second elongated electromagnetic radiation guide having an upwardly-facing end and a downwardly-facing free end disposed in close proximity to the free end of said at least one radiation guide, wherein said at least one liquid drop is formed at the free ends of the guides such that radiation from said at least one guide enters the free end of said second guide by internal reflection inside the at least one drop, and wherein said means for detecting comprises a detector coupled to the upwardly-facing end of said second radiation guide.

4. An apparatus according to claim 3, wherein said at least one and said second radiation guides are inclined from the vertical such that at their free ends the longitudinal axes thereof are disposed at an angle of between 18° and 22° with respect to one another.

5. An apparatus according to claim 1, wherein said means for directing electromagnetic radiation into said at least one guide is a light emitting diode.

6. An apparatus according to claim 1, wherein said means for directing electromagnetic radiation into said at least one guide is a laser.

7. An apparatus according to claim 1, wherein said apparatus further comprises means for modulating said electromagnetic radiation before it enters the at least one drop.

8. An apparatus according to claim 1, wherein said electromagnetic radiation is infra-red or visible light of wavelength in the range of 0.3 $\mu$m to 1.3 $\mu$m.

9. An apparatus according to claim 1, wherein said means for supplying liquid to be measured comprises means for causing a succession of drops to form at the free end of said at least one guide which drip from the at least guide.

10. An apparatus according to claim 9, wherein said means for causing a succession of drops to form comprises means for providing a constant head of said liquid.

11. An apparatus according to claim 1, wherein said means for supplying liquid and forming at least one drop of said liquid at the free end of said at least one radiation guide includes means for forming a single static drop of liquid at the free end of the at least one guide.

12. An apparatus according to claim 1, wherein said at least one electromagnetic radiation guide is an optical fibre.

13. A method for measuring a property of a liquid comprising the steps of:

providing at least one elongated electromagnetic radiation guide having a downwardly-facing free end and an upwardly-facing end, forming at least one drop of a liquid to be measured at the free end of said at least one guide at a position where radiation transmitted by the at least one guide can enter the at least one drop, directing electromagnetic radiation into the upwardly-facing end of said at least one guide for transmission therealong to the at least one drop of liquid formed at the free end thereof, and detecting the amplitude of radiation reflected internally of said at least one drop of liquid for deriving a signal which is a function of the interaction of the radiation with the liquid of the at least one drop.

* * * * *